(12) United States Patent
Schmidt et al.

(10) Patent No.: US 9,408,578 B2
(45) Date of Patent: Aug. 9, 2016

(54) TOPOGRAM FROM A SPIRAL RECONSTRUCTION

(71) Applicant: SIEMENS AKTIENGESELLSCHAFT, Munich (DE)

(72) Inventors: Bernhard Schmidt, Fuerth (DE); Martin Sedlmair, Forchheim (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 203 days.

(21) Appl. No.: 14/141,539

(22) Filed: Dec. 27, 2013

(65) Prior Publication Data

US 2014/0198894 A1    Jul. 17, 2014

(30) Foreign Application Priority Data

Jan. 11, 2013    (DE) .......................... 10 2013 200 337

(51) Int. Cl.
*A61B 6/03*    (2006.01)
*G06T 11/00*    (2006.01)
(Continued)

(52) U.S. Cl.
CPC ................ *A61B 6/032* (2013.01); *A61B 6/027* (2013.01); *A61B 6/4014* (2013.01); *A61B 6/542* (2013.01); *G06T 11/003* (2013.01); *G06T 11/005* (2013.01); *G06T 11/006* (2013.01)

(58) Field of Classification Search
CPC ...... A61B 6/027; A61B 6/032; A61B 6/4014; A61B 6/542
USPC ................................. 378/6, 7, 9, 15
See application file for complete search history.

(56) References Cited

U.S. PATENT DOCUMENTS

| 5,412,702 A | * | 5/1995 | Sata ....................... A61B 6/027 378/20 |
| 5,666,391 A | * | 9/1997 | Ohnesorge ........... A61B 6/5282 378/7 |

(Continued)

FOREIGN PATENT DOCUMENTS

| CN | 101249000 A | 8/2008 |
| CN | 102327124 A | 1/2012 |

(Continued)

OTHER PUBLICATIONS

DE Office Action dated Aug. 23, 2013.
(Continued)

*Primary Examiner* — Allen C. Ho
(74) *Attorney, Agent, or Firm* — Harness, Dickey & Pierce, P.L.C.

(57) ABSTRACT

A computed tomography system is disclosed, along with a method and computer program product. An embodiment uses such a spiral acquisition to reconstruct a spatial three-dimensional image of the examination region. The method also includes establishing a topogram of the examination region by parallel projection of the image along a projection direction. An embodiment of the invention allows distortion-free acquisition of a topogram, as a reconstructed spatial three-dimensional image can simply be projected in a parallel manner along a projection direction. An embodiment also allows multiple topograms to be established easily with just one acquisition, in that the reconstructed image of the examination region is projected in a parallel manner along different directions. An embodiment of the invention also allows particularly fast acquisition of a topogram, in particular in the clinical environment, as the rotating part of the gantry does not have to be stopped for the spiral acquisition.

14 Claims, 2 Drawing Sheets

(51) Int. Cl.
*A61B 6/02* (2006.01)
*A61B 6/00* (2006.01)

(56) References Cited

U.S. PATENT DOCUMENTS

| | | | | |
|---|---|---|---|---|
| 5,740,225 A * | 4/1998 | Nabatame | ............... | A61N 5/103 378/65 |
| 5,901,199 A * | 5/1999 | Murphy | ................... | A61B 6/08 378/65 |
| 6,470,067 B1 * | 10/2002 | Harding | ................. | A61B 6/032 378/19 |
| 6,480,561 B1 * | 11/2002 | Proksa | ................... | A61B 6/032 378/15 |
| 6,516,046 B1 * | 2/2003 | Frohlich | ................... | A61B 6/04 378/205 |
| 6,775,399 B1 * | 8/2004 | Jiang | ........................ | G06T 5/30 382/128 |
| 6,865,253 B2 * | 3/2005 | Blumhofer | ............. | A61B 6/547 378/205 |
| 6,876,719 B2 * | 4/2005 | Ozaki | .................... | A61B 6/032 378/4 |
| 7,145,980 B2 * | 12/2006 | Sakaguchi | ........... | A61B 6/4014 378/7 |
| 7,187,792 B2 * | 3/2007 | Fu | ........................ | A61N 5/1049 382/128 |
| 7,277,523 B2 * | 10/2007 | Mattson | ................. | A61B 6/032 378/15 |
| 7,366,279 B2 * | 4/2008 | Edic | ....................... | A61B 6/032 378/150 |
| 7,440,536 B2 * | 10/2008 | Bruder | .................. | A61B 6/032 378/4 |
| 7,443,945 B2 * | 10/2008 | Bruder | .................. | A61B 6/032 378/7 |
| 7,453,984 B2 * | 11/2008 | Chen | .................... | A61N 5/1049 378/65 |
| 7,522,779 B2 * | 4/2009 | Fu | ........................ | A61B 6/5235 278/54 |
| 7,535,987 B2 * | 5/2009 | Matsuda | ............... | G01N 23/046 378/159 |
| 7,623,617 B2 * | 11/2009 | Popescu | ................. | A61B 6/032 378/7 |
| 7,636,415 B2 * | 12/2009 | Popescu | ................. | A61B 6/032 378/7 |
| 7,680,241 B2 * | 3/2010 | David | .................... | A61B 6/032 378/7 |
| 7,751,525 B2 | 7/2010 | Ruhrnschopf | | |
| 7,873,141 B2 * | 1/2011 | Imai | ....................... | A61B 6/032 378/5 |
| 8,654,918 B2 * | 2/2014 | Eusemann | ............. | A61B 6/405 378/111 |
| 2001/0031032 A1 | 10/2001 | Proksa | | |
| 2008/0198965 A1 | 8/2008 | Popescu et al. | | |
| 2008/0260092 A1 | 10/2008 | Imai et al. | | |
| 2011/0317806 A1 | 12/2011 | Eusemann et al. | | |
| 2015/0023464 A1 | 1/2015 | Lou et al. | | |

FOREIGN PATENT DOCUMENTS

| | | |
|---|---|---|
| CN | 103315764 A | 9/2013 |
| DE | 102006045722 A1 | 4/2008 |
| DE | 102007008118 A1 | 8/2008 |
| EP | 1116475 A1 | 7/2001 |

OTHER PUBLICATIONS

Chinese Office Action issued in Chinese Patent Application No. 2013107500102 issued Sep. 2, 2015.

* cited by examiner

TOPOGRAM FROM A SPIRAL RECONSTRUCTION

PRIORITY STATEMENT

The present application hereby claims priority under 35 U.S.C. §119 to German patent application number DE 10 2013 200 337.4 filed Jan. 11, 2013, the entire contents of which are hereby incorporated herein by reference.

FIELD

At least one embodiment of the invention generally relates to a method and/or a computed tomography system for establishing a topogram, and/or to a computer program product.

BACKGROUND

Computed tomography is an imaging method used primarily for medical diagnosis. If a spatial three-dimensional image, or 3D image for short, of an examination region is to be acquired using computed tomography, the acquisition unit of a computed tomography system rotates about the examination region. The acquisition unit comprises an x-ray source and an x-ray detector. A projection is acquired at each of the different positions of the acquisition unit on its circular path. The different projections are acquired at different projection angles in this process. A projection angle in the following refers to a radial angle of the acquisition unit in its rotation plane; thus for example the angle formed by an x-ray source/x-ray detector connecting axis with a fixed axis parallel to the rotation plane. At the end of the series of acquisitions the projections are reconstructed to produce a 3D image.

The examination region is typically a defined body region of a patient. The examination region must be isolated before a high-resolution 3D image is acquired, to keep radiation exposure due to the plurality of projections as low as possible for the patient. To plan the acquisition of a high-resolution 3D image, an overview acquisition is produced in the form of a so-called topogram. The topogram is also used to determine the attenuation properties of the x-ray beams through the examination region, as the attenuation properties are used for the further determination of acquisition parameters for dose modulation during a further, in particular diagnostic, acquisition.

A conventional topogram is generally acquired in such a manner that the acquisition unit does not rotate and therefore only projections at a fixed projection angle are acquired. This means however that the rotational movement of the inner, rotatable part of the gantry, in which the x-ray source and x-ray detector are incorporated, must be slowed down. This slowing process generally takes 30 to 40 seconds and therefore represents a considerable delay in the clinical workflow. This delay can have serious consequences, in particular for patients suffering polytrauma after an accident.

Alternatively, a topogram can also be acquired in spiral mode, in that the inner part of the gantry rotates as for the acquisition of a high-resolution 3D image but the x-ray source operates in pulsed mode. Pulsed mode here means that the x-ray source only emits x-ray beams at a defined projection angle so that only projections. from a defined direction are acquired. This produces a "spiral topogram" which, like a conventional topogram, has a defined projection direction, for example anterior-posterior or lateral, for a patient. However the precise activation of the x-ray source proves difficult, so the x-ray source often also emits x-ray radiation when it is not required for the acquisition of a projection. This means that a higher dose is applied than is necessary for the acquisition of a topogram.

The acquisition of an individual topogram also only allows an overview at a defined projection angle, for example with anterior-posterior or lateral alignment in the case of a patient. In the case of a computed tomography system with just one x-ray source the acquisition of a second topogram at a different projection angle takes more time and also results in a higher dose for the patient. However it is important for dose modulation for a further acquisition after the topogram that the attenuation of the x-ray beams by the patient is determined along two body axes. In fact the attenuation properties of the examination region or of the patient are often estimated from just one topogram assuming an elliptical body cross section. This procedure is bound to be inaccurate and can therefore result in a higher dose being applied or poorer image quality than desired.

The projections for the cited methods for acquiring a topogram are central projections, as the x-ray beams spread in the shape of a fan or cone beam. The projection center here is the point at which the x-ray radiation is emitted by the x-ray source. This means that with the known methods for acquiring a topogram only central projections at a defined projection angle are acquired. There can therefore be no compensation for the distortions that occur with central projections, so the topograms resulting from the known methods have distortions.

SUMMARY

At least one embodiment of the invention provides a distortion-free topogram.

At least one embodiment of the invention is directed to a method, a computer program product, and/or a computed tomography system.

Embodiments of the invention are described below with respect to an apparatus and also with respect to a method. Features, advantages or alternative embodiments described here can also be applied to the other claimed subject matter and vice versa. In other words the object-related claims (which are directed at an arrangement for example) can also be developed using the features described or claimed in conjunction with a method. The corresponding functional features of the method here are formed by corresponding object-related modules.

At least one embodiment of the invention is based on a spiral acquisition of an examination region using a computed tomography system. At least one embodiment of the invention is based on the idea of using such a spiral acquisition to reconstruct a 3D image of the examination region and also of establishing a topogram of the examination region by parallel projection of the image along a projection direction. At least one embodiment of the invention allows the acquisition of a distortion-free topogram, as a reconstructed 3D image can simply be projected in a parallel manner along a projection direction. At least one embodiment of the invention also allows particularly fast acquisition of a topogram, in particular in the clinical environment, as the rotatable part of the gantry does not have to be stopped for the spiral acquisition.

In a further embodiment the invention comprises a computer program product with program code segments to execute the inventive method, when the computer program product is executed on a computer. This allows the individual steps of the method to be executed in a fast, identically repeatable and robust manner.

At least one embodiment of the invention can also be configured as a computed tomography system, comprising an acquisition unit, designed for the spiral acquisition of an examination region. At least one embodiment of the inventive computed tomography system further comprises a reconstruction unit, designed to reconstruct a 3D image of the examination region using spiral acquisition. At least one embodiment of the inventive computed tomography system also comprises an image processing unit, designed to establish a first topogram of the examination region by parallel projection of the image along a first projection direction. Such an inventive computed tomography system allows the acquisition of a distortion-free topogram.

BRIEF DESCRIPTION OF THE DRAWINGS

The invention is described and explained in more detail below based on the example embodiments illustrated in the figures, in which.

DETAILED DESCRIPTION OF THE EXAMPLE EMBODIMENTS

Figure 1:
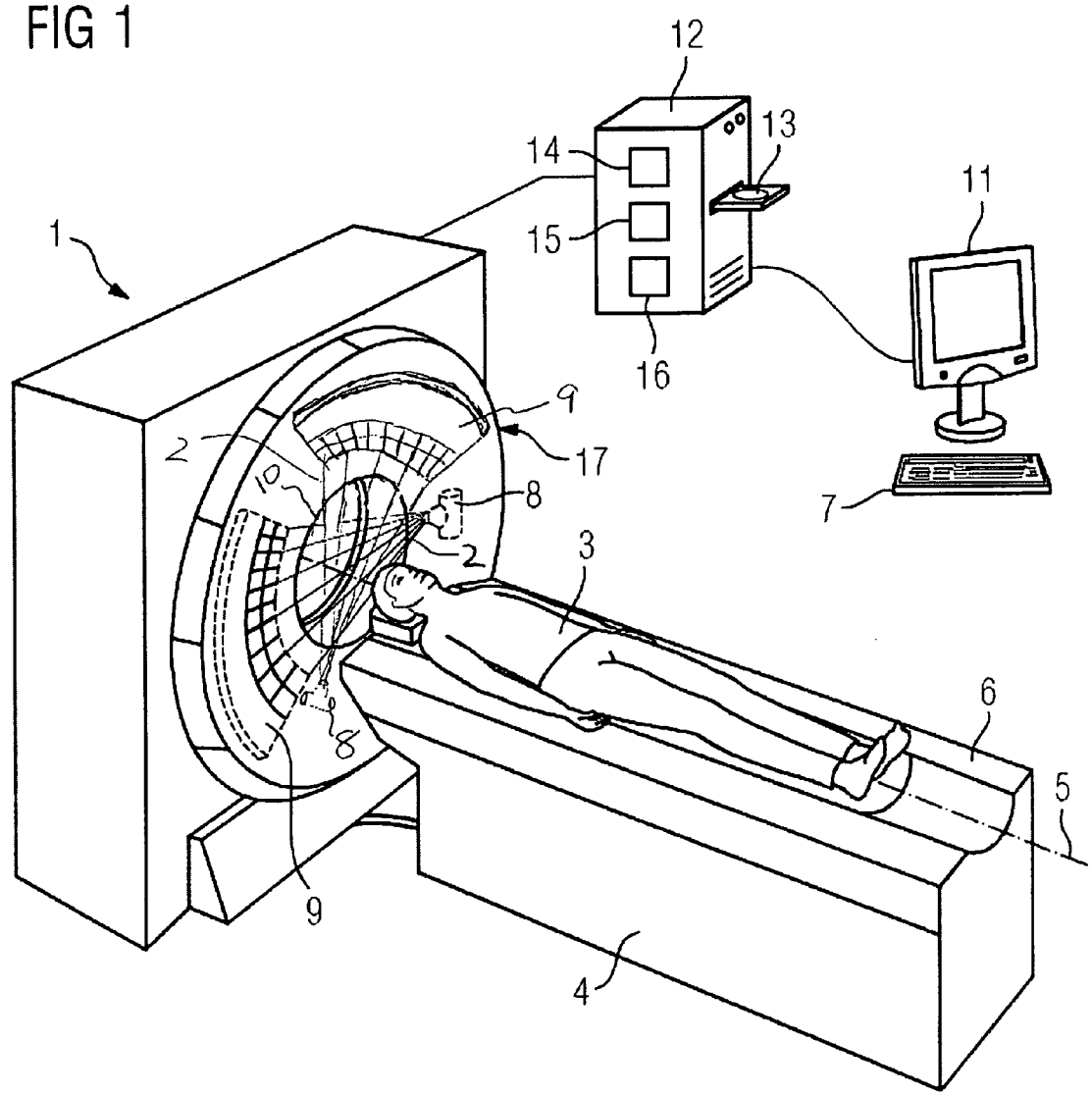
FIG. 1 shows an embodiment of an inventive computed tomography system.

At least one embodiment of the invention is based on a spiral acquisition of an examination region using a computed tomography system. At least one embodiment of the invention is based on the idea of using such a spiral acquisition to reconstruct a 3D image of the examination region and also of establishing a topogram of the examination region by parallel projection of the image along a projection direction. At least one embodiment of the invention allows the acquisition of a distortion-free topogram, as a reconstructed 3D image can simply be projected in a parallel manner along a projection direction. At least one embodiment of the invention also allows particularly fast acquisition of a topogram, in particular in the clinical environment, as the rotatable part of the gantry does not have to be stopped for the spiral acquisition.

Also multiple topograms can be established according to at least one embodiment of the invention with just one acquisition, in that the reconstructed image of the examination region is projected in a parallel manner along different projection directions. The different topograms supply different, complementary information content. The increased information content results from the volume scan using a spiral acquisition and the subsequent reconstruction of a 3D image.

According to a further aspect of at least one embodiment of the invention acquisition parameters for a further acquisition of the examination region are determined using at least one topogram.

According to a further aspect of at least one embodiment of the invention, the acquisition parameters are intensity values for the x-ray radiation for dose modulation for the further acquisition, the intensity values being determined using at least two topograms. Such determination allows the dose modulation to be performed particularly efficiently during a further acquisition.

According to a further aspect of at least one embodiment of the invention, the examination region in the image is segmented and scattering parameters of the examination region are determined based on the segmented image. The scattering parameters indicate the degree to which the irradiated x-ray radiation is scattered at a defined projection angle by the examination region. The scattering parameters therefore serve to correct the signal of the detected x-ray radiation in the individual projections by the scattered portion of the irradiated x-ray radiation. This also increases the quality of a 3D image, which is reconstructed from projections corrected using the scattering parameters.

If the spiral acquisition is based on a dose smaller than 200 µSv, the applied dose is particularly low.

In a further embodiment the invention comprises a computer program product with program code segments to execute the inventive method, when the computer program product is executed on a computer. This allows the individual steps of the method to be executed in a fast, identically repeatable and robust manner.

At least one embodiment of the invention can also be configured as a computed tomography system, comprising an acquisition unit, designed for the spiral acquisition of an examination region. At least one embodiment of the inventive computed tomography system further comprises a reconstruction unit, designed to reconstruct a 3D image of the examination region using spiral acquisition. At least one embodiment of the inventive computed tomography system also comprises an image processing unit, designed to establish a first topogram of the examination region by parallel projection of the image along a first projection direction. Such an inventive computed tomography system allows the acquisition of a distortion-free topogram.

According to at least one embodiment of the invention, the image processing unit is also designed to establish at least one second topogram of the examination region by parallel projection of the image along at least one second projection direction. The different topograms supply different, complementary information content.

According to a further aspect of at least one embodiment of the invention the image processing unit is also designed to segment the examination region in the image.

According to a further aspect of at least one embodiment of the invention the computed tomography system comprises a determination unit, which is designed to determine acquisition parameters for a further acquisition of the examination region using at least one topogram.

According to a further aspect of at least one embodiment of the invention the determination unit is also designed to determine scattering parameters using the segmented image.

According to a further aspect of at least one embodiment of the invention the computed tomography system has two x-ray sources and two x-ray detectors respectively. This allows a particularly fast spiral acquisition for establishing an inventive topogram.

According to a further aspect of at least one embodiment, the invention comprises an inventive computed tomography system as well as a computer, into which the inventive computer program product can be loaded.

Within the context of at least one embodiment of the present invention a topogram is understood to mean a two-dimensional overview acquisition of an examination region, acquired using a computed tomography system. A topogram is a projection of the examination region. A topogram allows the part of the examination region of relevance for a further, in particular diagnostic, acquisition to be identified.

An examination region is essentially understood to mean any body region of a patient, in particular the thorax, abdomen or legs. The examination region can in particular comprise organs such as the heart, kidney or liver.

A diagnostic acquisition or an acquisition of a diagnostic image is understood to mean an acquisition of the examination region (or part thereof) using a computed tomography system, the diagnostic image or the image resulting from the diagnostic acquisition having a quality that is adequate for investigation and subsequent diagnosis. The quality of an acquisition or image in particular takes into account the signal-to-noise ratio and the spatial resolution of the resulting image. Generally a diagnostic acquisition is a volume scan which allows the reconstruction of a 3D image. A diagnostic acquisition using computed tomography generally requires a dose of more than 1 mSv. Investigation and diagnosis comprise the identification of morbid changes, for example hemorrhages, tumors, changes to organ structures or plaque formation in blood vessels.

The acquisition parameters are parameters which facilitate a further, in particular diagnostic, acquisition. In particular the acquisition parameters can be position values, which isolate precisely the part of the examination region for which a diagnostic image is to be produced. The acquisition parameters can also be intensity values for the x-ray radiation for dose modulation for a further acquisition. Such intensity values can in particular be a function of the projection angle. The intensity values result specifically from the activation of the x-ray source, in other words for example the activation of the current or voltage of an x-ray tube. The intensity values are obtained from the attenuation properties of the examination region, which indicate the degree to which a part of the examination region attenuates x-ray radiation in a defined direction. The attenuation properties can be obtained directly from a topogram. The acquisition parameters can also comprise settings for filters or diaphragms.

Within the context of at least one embodiment of the invention a dose is understood to mean the dose of energy, in other words the energy of the radiation, which a patient absorbs per kg of body weight. A dose defined in this manner is generally given in Sievert units, or Sv for short.

The acquisition unit comprises at least one x-ray source as well as an x-ray detector. The x-ray source is for example an x-ray tube. The x-ray detector is for example a line detector with multiple lines. However the x-ray detector can also be configured as a flat panel detector. The x-ray detector is generally configured as a scintillator counter, in which the high-energy x-ray photons are converted by way of a scintillator to low-energy photons in the optical spectrum and then detected by means of a photodiode. Alternatively the x-ray detector can be configured as a direct conversion detector, which converts the high-energy x-ray photons directly to an electric signal current by means of internal photostimulation using a semiconductor material based on the photovoltaic principle.

The reconstruction unit, the image processing unit and the determination unit can each be configured in both hardware or software form. The units are each configured for example as a so-called FPGA (acronym for field programmable gate array) or each comprise an arithmetic logic unit. Multiple units can also be configured in the form of a uniform computer program product. For example the image processing unit and the determination unit can be configured as an executable computer program product. Also a computer, on which a computer program product is stored in an executable manner or on which a computer program product is executed, can also itself be part of the respective unit.

FIG. 1 shows an embodiment of an inventive computed tomography system. The computed tomography system shown here has an acquisition unit 17, comprising an x-ray source 8 as well as an x-ray detector 9. The acquisition unit 17 rotates during the spiral acquisition for an embodiment of the inventive establishing of a topogram about a longitudinal axis 5, and the x-ray source 8 emits an x-ray fan beam 2 during the spiral acquisition. In the example shown here the x-ray source 8 is an x-ray tube. In the example shown here the x-ray detector 9 is a line detector with multiple lines.

During the acquisition of an image using an embodiment of the inventive computed tomography system, in particular during the acquisition of a topogram or a diagnostic image, the patient 3 lies on a patient support 6. The patient support 6 is connected to a support base 4 in such a manner that it supports the patient support 6 and the patient 3. The patient support 6 is designed to move the patient 3 along an acquisition direction through the opening 10 of the acquisition unit 17. The acquisition direction is generally defined by the longitudinal axis 5, about which the acquisition unit 17 rotates during the spiral acquisition for an embodiment of the inventive establishing of a topogram. However the longitudinal axis 5 can also be tilted in relation to the acquisition direction, along which the patient 3 is moved during the acquisition, for example in that the acquisition unit 17 is configured as part of a tiltable gantry 1.

During a spiral acquisition the patient support 6 is moved continuously through the opening 10, while the acquisition unit 17 rotates about the patient 3 and acquires projections. The x-ray fan beam 2 therefore describes a spiral on the surface of the patient 3. Spiral acquisition is a widely used mode for acquiring diagnostic images, as it allows a volume scan of a defined examination region—or even the whole patient 3—to be performed quickly. Such a volume scan is a prerequisite for the reconstruction of a high-resolution 3D image, as is generally required for diagnostic purposes.

The individual x-ray projections are acquired in the form of central projections, as the x-ray beams spread in a fan shape from a projection center in the form of the exit window of the x-ray tube. Central projections are not truly parallel and therefore have distortions. The length ratios of a projected examination region can deviate from the true length ratios of the examination region with a central projection.

The distortions due to a central projection cannot be compensated for with a conventional acquisition method for a topogram, in which the examination region is only acquired at a fixed projection angle. In contrast during the reconstruction of a 3D image based on a spiral acquisition algorithms are used, which allow a distortion-free display of the examination region. It is however a prerequisite for the use of such algorithms that a volume scan is available but such a volume scan is not available for a topogram with conventional acquisition methods.

To establish a topogram, an embodiment of the invention is therefore based on a spiral acquisition of an examination region, as the volume scan of the examination region using the spiral acquisition allows the reconstruction of a 3D image of the examination region and therefore the establishing of a topogram of the examination region by parallel projection of the reconstructed image along a projection direction. Parallel projection takes place here on the plane of the already reconstructed image.

An embodiment of the invention therefore allows distortion-free acquisition of a topogram. Distortion-free here means that the resulting topogram is truly parallel and maintains the length ratios.

The projection direction of the parallel projection can also be selected freely; for example a lateral or an anterior-posterior topogram may be required. An embodiment of the invention therefore has greater flexibility than conventional methods for acquiring a topogram.

The greater flexibility is also demonstrated in that it is very easy to use different projection modes to establish a topogram. For example the parallel projection of the reconstructed image can take place in the form of a projection of the maximum values or the standard deviation of the values in the projected image volume. The projection mode can be selected freely based on the current issue and the examination region.

An embodiment of the inventive establishing of different topograms in different projection directions only requires a single spiral acquisition, as a plurality of different topograms can be established by parallel projections along different projection directions from a single reconstructed 3D image. This makes an embodiment of the inventive establishing of different topograms of an examination region particularly fast compared with multiple conventional acquisitions of individual topograms.

In the clinical environment, in particular, an embodiment of the invention allows particularly fast acquisition of a topogram, as the rotatable part of the gantry 1 does not have to be stopped for the spiral acquisition. A switch between an acquisition for diagnostic purposes, during which the inner part of the gantry 1 rotates, and a conventional acquisition of a topogram, during which the inner part of the gantry 1 does not rotate, takes 30 to 40 seconds and such a delay can have serious consequences, in particular for a patient 3 suffering polytrauma after an accident.

To allow the fastest possible spiral acquisition, the greatest possible pitch should be used. The pitch p=V/B results from the relationship between the advance V of the patient support 6 per 360° rotation of the acquisition unit 17 and the collimated width B of the x-ray fan beam 2 along the longitudinal axis 5. A large pitch is for example a pitch of 1.5 to 2 in the case of an acquisition unit 17 with a single x-ray source 8 and a single x-ray detector 9.

The speed of the spiral acquisition, on which an embodiment of the inventive establishing of a topogram is based, can also be increased by means of a so-called dual source acquisition unit. A dual source acquisition unit has two x-ray sources 8 and two x-ray detectors 9, so that during a spiral acquisition the examination region can be irradiated simultaneously at different projection angles. The simultaneous acquisition of two projections at different projection angles means that the pitch can be increased during the spiral acquisition with a dual source acquisition unit compared with an acquisition unit 17 with just a single x-ray source 8. Thus a pitch greater than 3 is possible with a dual source acquisition unit.

It is also desirable for the applied dose to be particularly small during the spiral acquisition for an embodiment of the inventive establishing of a topogram. Because the requirements relating to the quality of the reconstructed 3D image, from which an embodiment of the inventive topogram is established, are not as stringent as the requirements relating to a diagnostic image, in particular not in respect of the spatial resolution and signal-to-noise ratio, a lower dose can also be applied during the spiral acquisition for an embodiment of the inventive establishing of a topogram than during an acquisition of a diagnostic image. In particular the applied dose during the spiral acquisition for an embodiment of the inventive establishing of a topogram can be smaller than 1 mSv but it can also be smaller than 200 μSv or smaller than 100 μSv.

If dose modulation is already applied for the spiral acquisition for an embodiment of the inventive establishing of a topogram, the applied dose is particularly small. Dose modulation can take place in particular in real time, in other words in that attenuation properties are determined continuously during the spiral acquisition and used to derive the dose or intensity of the x-ray radiation to be applied. With dose modulation of a spiral acquisition in real time the intensity of the x-ray radiation is controlled for example with a 180° offset. The intensity of the x-ray radiation is therefore calculated on the basis of attenuation properties, which are based on a segment of the spiral acquisition acquired with a 180° offset. This procedure is based on the assumption of a certain symmetry of the examination region.

An embodiment of the invention has the further advantage that the spiral acquisition for the inventive establishing of a topogram can also be used to generate further views. A multiplanar reconstruction for example allows slice images of the examination region that are disposed in any manner to be generated. A 3D surface view of the examination region can also be provided by rendering. This increases the clinical benefit of an embodiment of the inventive method compared with conventional methods for acquiring a topogram. In individual instances such a further view can even render a diagnostic acquisition superfluous.

Acquisition parameters for a further, in particular diagnostic, acquisition of the examination region can also be determined with an embodiment of the inventively established topogram. Such acquisition parameters can be in particular intensity values for the x-ray radiation for dose modulation for a further acquisition, the intensity values being determined using at least two topograms. The determination of such intensity values is important in order to perform dose modulation as efficiently as possible during a further acquisition. During dose modulation the dose or intensity of the x-ray radiation is modified as a function of the projection angle. To achieve the most isotropic image quality possible in an image, it is necessary, for example for a patient 3 of normal weight, to apply a higher dose in the lateral direction in the shoulder region than in the anterior-posterior direction.

In order for precisely the correct dose or intensity of x-ray radiation to be determined and then applied, as required to achieve a defined image quality along a defined projection direction, the attenuation properties of the examination region must be known along this defined projection direction. It is possible to derive the attenuation properties along different projection directions directly from an embodiment of the inventively established topograms. An embodiment of the invention therefore allows particularly efficient dose modulation of a further, in particular diagnostic, acquisition, as it is no longer necessary to estimate the attenuation properties, for example assuming an elliptical body cross section. There is therefore no need for dose modulation in real time during a further acquisition.

It is also possible to determine scattering parameters of the examination region and acquisition parameters for a further acquisition of the examination region by segmenting S the examination region in the reconstructed image. By segmenting S the reconstructed 3D image it becomes possible to calculate the surface or envelope of the examination region. Current rendering methods can be used to display the segmented examination region. The scattering parameters indicate the degree to which the irradiated x-ray radiation is scattered at a defined projection angle by the examination region. The scattering parameters therefore serve to correct the signal of the detected x-ray radiation in the individual projections by the scattered portion of the irradiated x-ray radiation. This also improves the quality of a 3D image reconstructed from projections corrected using the scattering parameters.

The determination of scattering parameters based on a segmented examination region only took place until now after a high-resolution 3D acquisition, for example to correct beam hardening. An embodiment of the inventive method allows the scattering parameters to be determined before the high-resolution 3D acquisition. This not only accelerates the clinical workflow but the acquisition parameters can also be improved for a further image taking into account the scattering parameters. For example the voltage of the x-ray tube can be adjusted, if the examination region contains a metal implant which scatters and absorbs x-ray radiation to a particularly significant degree.

Segmentation S takes place for example using a threshold value method or a region-based method such as so-called region growing or region splitting or with the aid of edge extraction.

The scattering parameters can also be determined without segmentation S, using a dual source acquisition unit. Also just one of the two x-ray sources 8 of the dual source acquisition unit can emit x-ray radiation during the spiral acquisition for the inventive establishing of a topogram, while both x-ray detectors 9 detect the x-ray radiation penetrating through the examination region or scattered by the examination region. The first x-ray detector 9 is therefore used for the acquisition of individual x-ray projections, while the second x-ray detector 9 is used for the detection of a portion of the scattering radiation. Scattering parameters can then be derived from the signal of the scattering radiation detected by the second x-ray detector 9. The invention is also advantageous when a dual source acquisition unit is used, because it allows better consideration of the scattered, detected x-ray radiation during the reconstruction of a further image of the examination region acquired using the two x-ray detectors 9.

To perform an embodiment of the inventive method, an embodiment of the inventive computed tomography system has a reconstruction unit 14, designed to reconstruct a 3D image of the examination region using the spiral acquisition. An embodiment of the inventive computed tomography system also has an image processing unit 15, designed to establish multiple topograms of the examination region by way of parallel projections of the reconstructed image along different projection directions. An embodiment of the inventive computed tomography system also has a determination unit 16, designed to determine acquisition parameters for a further acquisition of the examination region using at least one topogram. The reconstruction unit 14, the image processing unit 15 and the determination unit 16 in the example shown here are configured as computer programs, in other words as software, which can be stored in an executable manner in each instance on a computer 12. The data of the individual projections is transmitted from the gantry 1 of the computed tomography system to the computer 12 for reconstruction or further processing.

The reconstruction unit 14 and the image processing unit 15 are also designed to process the acquired data in real time and forward it to an output unit 11. Thus for example the slice images of the examination region reconstructed during a spiral acquisition can be displayed directly on the output unit 11.

The computer 12 is connected to an output unit 11 and an input unit 7. The output unit 11 is for example one (or more) LCD, plasma or OLED screen(s). Outputting on the output unit 11 involves for example a graphical user interface for the manual inputting of patient data and for activating the individual units of the computed tomography system and for selecting acquisition parameters. Different views of the acquired data, in other words topograms, modified surfaces, or slice images can also be displayed on the output unit 11. The input unit 7 is for example a keyboard, mouse, touch screen or even a microphone for voice input.

An embodiment of the inventive method can also be executed using a computer program product. To this end, the computer program product has program code segments for executing the method, when the program product is executed on a computer 12. The computer program product can be designed for example to be loaded into a processor and/or the working memory of a programmable computer 12. The computer program product can also be configured in the form of an executable file, which is stored for example on the computer 12 or on a server. The computer program product can also be stored on a computer-readable medium 13 such as for example a CD, a portable hard drive or a USB stick. For the different embodiments of the computer program product the computer 12 must have the respective requisites such as for example a corresponding working memory, a corresponding graphics card or a corresponding logic unit, so that the respective method steps can be executed efficiently.

Figure 2:
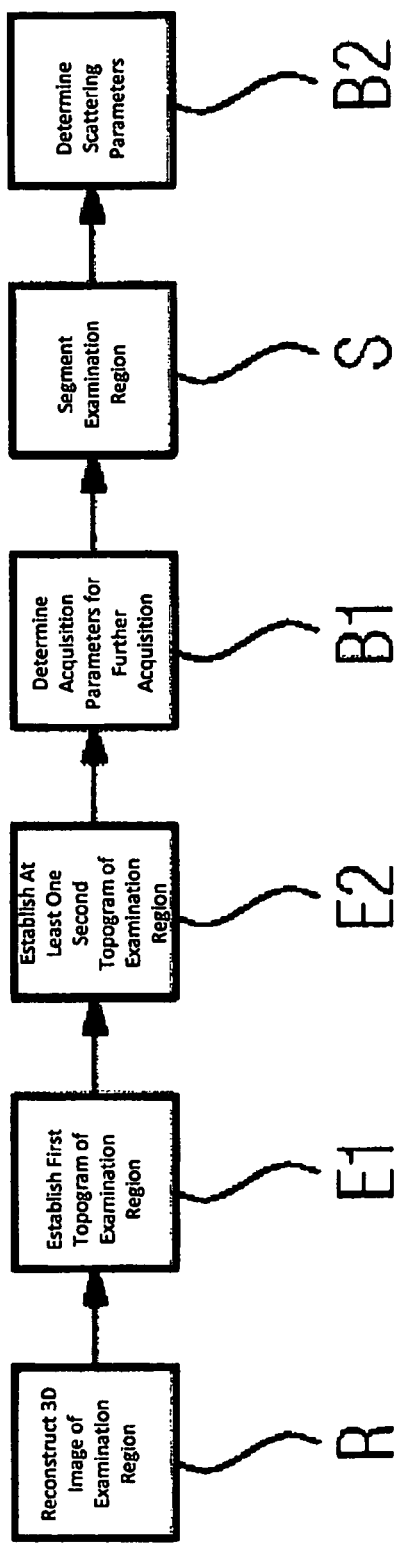
FIG. 2 shows a flow diagram of an embodiment of the inventive method.

FIG. 2 shows a flow diagram of an embodiment of the inventive method. The steps of an embodiment of the inventive method shown here and already described in more detail in FIG. 1, based on a spiral acquisition of an examination region using a computed tomography system, are as follows:

reconstruction R of a 3D image of the examination region using the spiral acquisition, first establishing E1 of a first topogram of the examination region by a parallel projection of the image along a first projection direction, second establishing E2 of at least one second topogram of the examination region by a parallel projection of the image along at least one second projection direction, first determination B1 of acquisition parameters for a further acquisition of the examination region using at least one topogram, segmentation S of the examination region in the image, second determination B2 of scattering parameters using the segmented image.

The spiral acquisition of an examination region using a computed tomography system can itself be configured as a step of an embodiment of the inventive method. This applies in particular to spiral acquisitions with a particularly large pitch greater than 1.5 (for an acquisition unit 17 with one x-ray source 8) or greater than 3 (for an acquisition unit 17 with two x-ray sources 8) as well as for spiral acquisitions with a particularly low dose of less than 200 µSv or less than 100 µSv.

What is claimed is:

1. A method for establishing a topogram, based on a spiral acquisition of an examination region using a computed tomography system, the method comprising:
reconstructing a spatial three-dimensional image of the examination region using the spiral acquisition;
establishing a first topogram of the examination region by a parallel projection of the spatial three-dimensional image along a first projection direction;
computing an envelope of the examination region by segmenting the examination region in the spatial three-dimensional image; and
determining scattering parameters based on the computed envelope of the segmented examination region.

2. The method of claim 1, further comprising:
establishing at least one second topogram of the examination region by a parallel projection of the spatial three-dimensional image along at least one second projection direction.

3. The method of claim 2, further comprising:
determining acquisition parameters for a further acquisition of the examination region using at least one of the first topogram and the second topogram.

4. The method of claim 3, wherein the acquisition parameters are intensity values for x-ray radiation for dose modulation for the further acquisition, the method further including:

determining the intensity values using at least the first topogram and the second topogram.

5. The method of claim 1, further comprising:
determining acquisition parameters for a further acquisition of the examination region using at least the first topogram.

6. The method of claim 5, wherein the acquisition parameters are intensity values for x-ray radiation for dose modulation for the further acquisition, and the method further includes
determining, the intensity values using at least the first topogram.

7. The method of claim 1, further comprising:
applying a spiral acquisition with a dose smaller than 200 μSv during the spiral acquisition.

8. A non-transitory computer-readable storage medium including program code segments that, when executed, cause a computer to execute the method of claim.

9. A computed tomography system for establishing a topogram, the computed tomography system comprising:
an acquisition unit, including an x-ray source and an x-ray detector, designed for a spiral acquisition of an examination region;
a reconstruction unit, configured to reconstruct a spatial three-dimensional image of the examination region using the spiral acquisition;
an image processing unit, configured to
establish a first topogram of the examination region by a parallel projection of the spatial three-dimensional image along a first projection direction, and
compute an envelope of the examination region by segmenting the examination region in the spatial three-dimensional image; and
a determination unit, configured to determine scattering parameters based on the computed envelope of the segmented examination region.

10. The computed tomography system of claim 9, wherein the image processing unit is further configured to establish at least one second topogram of the examination region by a parallel projection of the spatial three-dimensional image along at least one second projection direction.

11. The computed tomography system of claim 10, further comprising:
a determination unit, configured to determine acquisition parameters for a further acquisition of the examination region using at least one of the first topogram and the second topogram.

12. The computed tomography system of claim 9, further comprising:
a determination unit, configured to determine acquisition parameters for a further acquisition of the examination region using at least the first topogram.

13. The computed tomography system of claim 9, wherein the acquisition unit further includes a second x-ray source and a second x-ray detector.

14. A computed tomography system for establishing a topogram, the computed tomography system comprising:
an acquisition unit, including an x-ray source and an x-ray detector, designed for a spiral acquisition of an examination region;
a reconstruction unit, configured to reconstruct a spatial three-dimensional image of the examination region using the spiral acquisition;
an image processing unit, configured to establish a first topogram of the examination region by a parallel projection of the image along a first projection direction; and
a computer, into which the program code segments included in the non-transitory computer-readable storage medium of claim 8 are loadable.

* * * * *